United States Patent [19]

Prengler

[11] Patent Number: 5,451,201
[45] Date of Patent: Sep. 19, 1995

[54] JOINT SUPPORT APPARATUS

[75] Inventor: Randall Prengler, Dallas, Tex.

[73] Assignee: Innovative Footwear Corporation, Dallas, Tex.

[21] Appl. No.: 164,059

[22] Filed: Dec. 8, 1993

Related U.S. Application Data

[63] Continuation-in-part of Ser. No. 949,973, Sep. 24, 1992, abandoned.

[51] Int. Cl.$^6$ ................................. A61F 5/00
[52] U.S. Cl. .............................. 602/26; 602/13
[58] Field of Search ................ 602/5, 6, 13, 20, 26, 602/23, 27, 60-65; 2/16, 22-24

[56] References Cited

U.S. PATENT DOCUMENTS

| | | | |
|---|---|---|---|
| 4,219,892 | 9/1980 | Rigdon | 602/26 X |
| 4,250,578 | 2/1981 | Barlow | 602/26 X |
| 4,287,885 | 9/1981 | Applegate | 602/26 |
| 4,378,009 | 3/1983 | Rowley et al. | 602/13 |
| 4,682,587 | 7/1987 | Curlee | 602/13 |
| 4,872,448 | 10/1989 | Johnson, Jr. | 602/13 X |
| 4,938,207 | 7/1990 | Vargo | 602/26 |

Primary Examiner—Linda C. M. Dvorak
Attorney, Agent, or Firm—Jones, Day, Reavis & Pogue

[57] ABSTRACT

A joint support apparatus for wrapping around a joint to protect and support the joint during sports-like or sports-related activities. The main body of the apparatus being made of at least one sheet of flexible resilient material and constructed to urge the knee-joint to maintain a partially flexed position. The apparatus may also include a specially positioned pad to account for natural curvature of the knee-joint to maintain a more balanced support to the joint particularly during extension. Further the apparatus may also include an inflatable bladder.

11 Claims, 4 Drawing Sheets

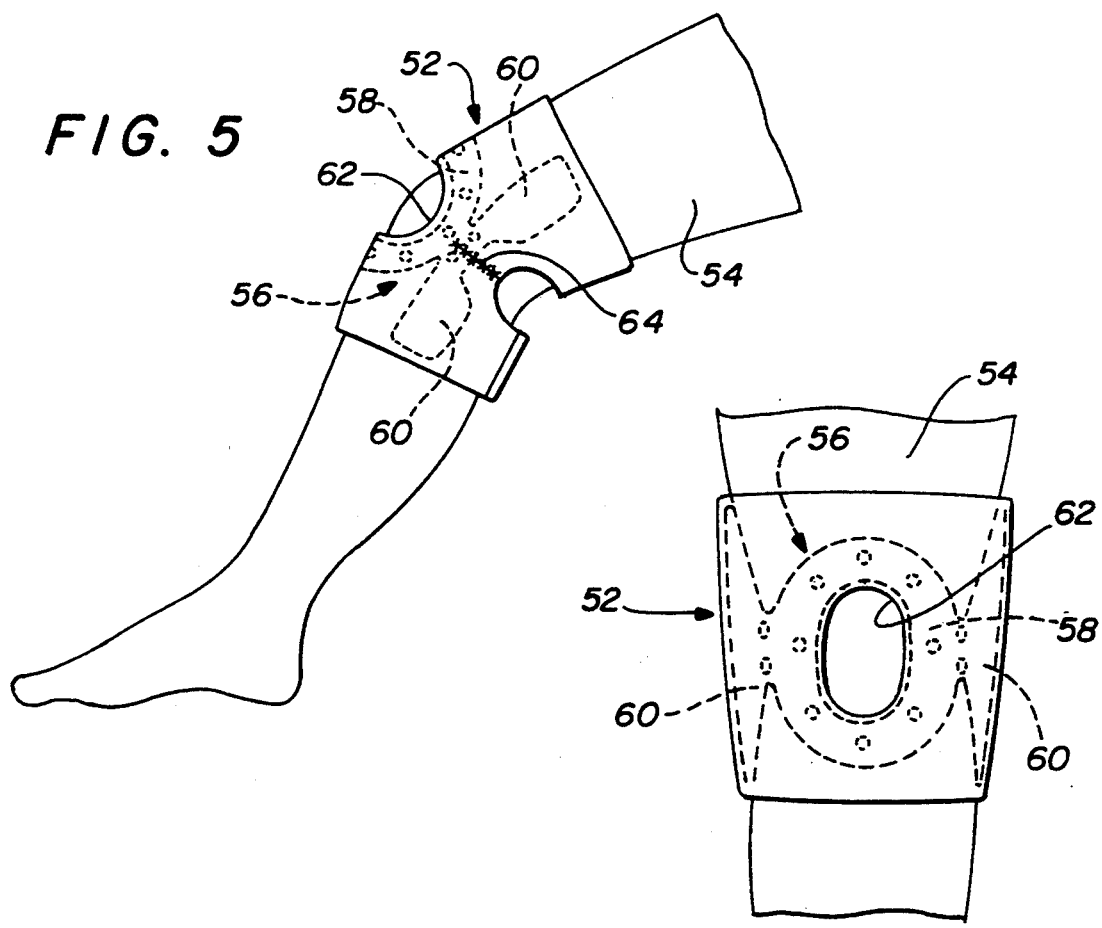
FIG. 5
FIG. 6
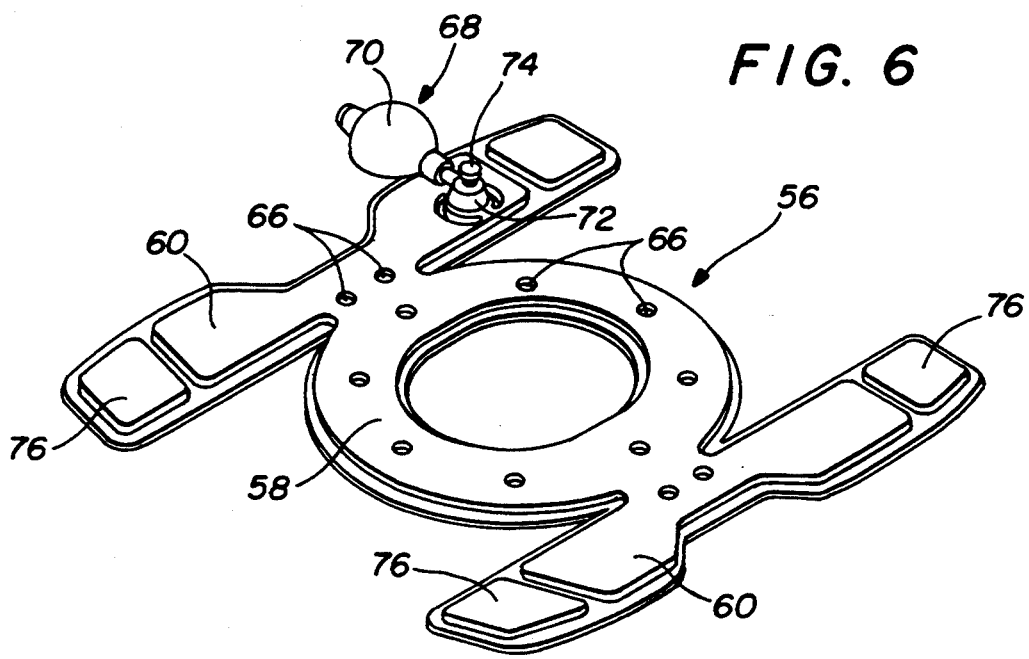
FIG. 7

JOINT SUPPORT APPARATUS

This is a continuation-in-part of application Ser. No. 07/949,973 filed Sep. 24, 1992 entitled Knee-Joint Support Apparatus, now abandoned.

BACKGROUND OF THE INVENTION

1. Field of the Invention

The present invention relates generally to orthopedic or orthotic apparatuses and more specifically to joint support apparatuses which do not prevent the movement of the joint but provide support and added resistance to movement of the joint in sports-like or sports-related activities.

2. Description of Related Art

A joint, such as the knee-joint, has been frequently described and modeled as a ginglymus or hinged joint. In actuality, the knee-joint is much more complicated. A better model of the joint is a combination of two condyloid joints which, like a ball and socket, allow flexion, extension, abduction, adduction and circumduction, but not axial rotation; and one almost arthrodial joint which, like a rail and bearing, allows gliding motion. The condyloid joints are between the Femur and the Tibia. The combination of two (2) condyloid joints limits the abduction, adduction, and circumduction of a joint when aligned side by side. The movement of the knee-joint is also partially restricted by the arthrodial like joint between the Patella, knee-cap, and the Femur. All three (3) joints that comprise the knee-joint are held together and partially restricted by a complex system of ligaments and cartilages.

In addition to playing a role in restricting its range of motion, the Patella plays several other important roles in the articulation of the knee-joint. The Patella serves as an extension to the lever arm by which the quadriceps extends the knee-joint. The Patella also serves to protect the anterior of the knee-joint, of which it is apart.

Many attempts have been made to model the movement of the knee-joint and design a support based on that model. Many of these support systems are designed to support only a portion of the knee-joint mechanism. For example, see Shiono, U.S. Pat. No. 5,024,216, which is purportedly designed to prevent Patellar instability or dislocation. See also Skwor et al., U.S. Pat. No. 5,042,464; Karczewski, U.S. Pat. No. 4,651,722; and Nelson U.S. Pat. No. 4,366,813; which support the knee-joint against lateral movement. Some of the earlier support devises, such as Stubbs, U.S. Pat. No. 3,463,147, supported the knee-joint by providing added resistance to flexion.

In addition, many attempts have been made to add inflatable tubes or bladders to joint braces to provide additional cushioning and support to a user's joints. One such example is disclosed in a patent to Rowley et al., U.S. Pat. No. 4,378,009, which discloses multiple embodiments of inflatable joint braces for joints such as the knee and wrist. In particular, a knee brace is disclosed having a plurality of interconnected tubes which cross over from one side of the knee to the other in a diagonal manner and from an upper portion to a lower portion to substantially surround the knee. It would be advantageous to provide a joint brace that provides cushioning to the joint as well as lateral support. Another example is a patent to Johnson, U.S. Pat. No. 4,628,945 that discloses inflatable liners within molded plastic shell members placed on either side of a user's ankle. It would be advantageous to provide a joint brace that provides cushioning and support to the foot and ankle while still allowing significant freedom of movement for sports-related activities.

SUMMARY OF THE INVENTION

Briefly, one embodiment of the present invention provides a new joint support apparatus constructed from a flat I-beam shaped sheet of flexible and resilient material. The support is angled by closing notches in both sides of the I-beam shaped sheet by connecting the sides of the notches. The knee-joint support includes connectors which connect the sides of the flanges of the I-beam shaped sheet after they are wrapped around the limb of a user.

Another embodiment of the present invention also includes a pad attached to the inner surface of the flat I-beam shaped sheet of flexible and resilient material which serves to increase the support of the arthrodial joint by filing a gap caused by the natural curvature of the knee during extension and providing additional protection from impact injury.

Still another embodiment of the present invention discloses a brace for joints such as the elbow or knee that includes an integral inflatable bladder portion. The bladder includes a pair of elongated stay portions that are applied to opposite sides of a user's limb for providing lateral support to that limb at the joint where the brace is attached.

It is, therefore, an object of the present invention to provide a joint brace to protect the constituent elements of the joint.

It is another object of the present invention to provide a joint brace with an inflatable bladder integral to the joint brace wherein the brace includes a pair of elongated stays for providing lateral support to a user's joint.

BRIEF DESCRIPTION OF THE DRAWINGS

These and other objects and features of the present invention will become fully apparent from the following detailed description of the preferred embodiment in conjunction with the drawings.

FIG. 5 illustrates a side view of an alternative embodiment of the present invention for a knee-joint pad using an inflatable bladder.

FIG. 6 illustrates a front view of the embodiment of FIG. 5.

FIG. 7 is an illustration of the inflatable bladder of FIGS. 5 and 6.

DESCRIPTION OF THE PREFERRED EMBODIMENT

Reference is now made to the figures, wherein like parts are designated with like numerals throughout.

Figure 1:
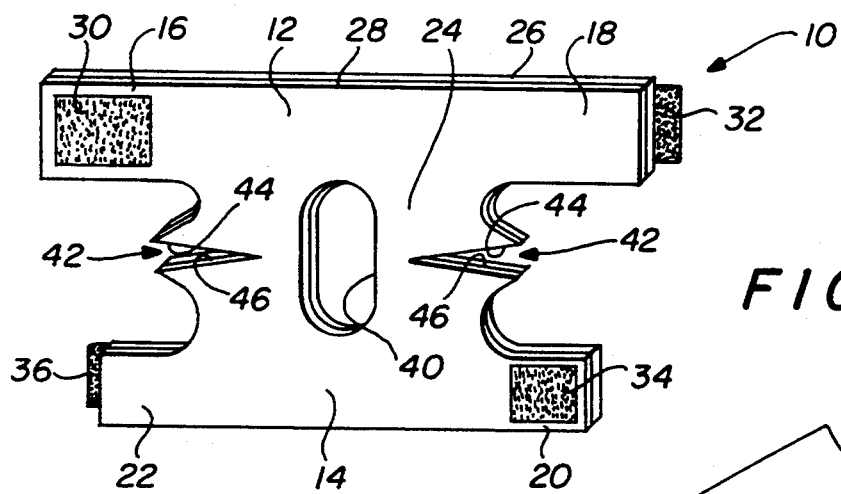
FIG. 1 illustrates a top oblique view of the main body of the knee-joint support prior to complete construction.

FIG. 1 illustrates the main body 10 of the knee-joint support invention prior to completion. The main body 10 of the support is generally shaped like the cross-section of an I-beam with an upper flange 12 and a lower flange 14. The upper flange 12 is noticeably longer than the lower flange 14 since the thigh, which the upper flange 12 wraps around during use, has a larger circumference than the circumference of the calf, around which the lower flange 14 wraps. Bridging between the upper flange 12 and lower flange 14 is a web structure 24. Both flanges 12 & 14 have a left and right side 16, 18, 20, and 22.

The main body 10 of the support is preferably constructed of a flexible and resilient material. More specifically, the preferred embodiment of the construction of the main body 10 is a two layered material: an inner layer 26 preferably made of a material with the qualifies similar to neoprene foam rubber, lending flexibility, resilience, and padding for comfort and protection from impact, and an outer layer 28 preferably made of a woven elastic material.

Connector means 30 & 32, and 34 & 36 are attached to the sides of the flanges 16, 18, 20, and 22. These connector means 30 & 32, and 34 & 36 are preferably hook & pile connectors more commonly known as Velcro ®. FIG. 1 illustrates the main body 10 of the knee-joint support from a top oblique view, the hook halves 30 and 34 of the hoop & pile connectors are illustrated on top while only the protruding portion of the pile halves 32 and 36 of the hoop & pile connectors are shown. It is preferable that the pile halves 32 and 36, of the hook & pile connectors protrude from the main body 10 for ease of use. It is also preferable that the hook & pile connectors 30 & 32, and 34 & 36 be opposed, as illustrated, so that one flange's sides 16 and 18, or 20 and 22 are connected left over fight while the other flanges' sides 20 and 22, or 16 and 18 respectively, are connected right over left. The opposing overlap of the flange sides 16, 18, 20, and 22 is shown in FIG. 2 at 40 and results in a more symmetrical support of the knee-joint.

FIG. 1 also illustrates the preferred embodiment of an aperture 40 approximately in the center of the web structure 24. The aperture 40 is designed to accept the Patella of the knee-cap and allow for the relatively unencumbered movement of the Patella along the gliding path of the arthrodial joint.

Also illustrated in FIG. 1 are notches 42 in the sides of the web structure 24. The notches 42 are each comprised of two surfaces 44 and 46. Although the notches 42 should be generally "V" shaped, variations from a straight lined "V" are possible as long as the notch surfaces 44 and 46 remain generally symmetric or equal in length. The notch surfaces 44 and 46 should remain relatively symmetric because during construction of the knee-joint support, these surfaces 44 and 46 of the main body 10 are connected by some means, such as sewn, in a manner that allows the main body 10 to retain its flexibility and resilience characteristics along the joint 48 formed between the two surfaces of the notch 44 and 46 as shown in FIG. 2.

Figure 2:
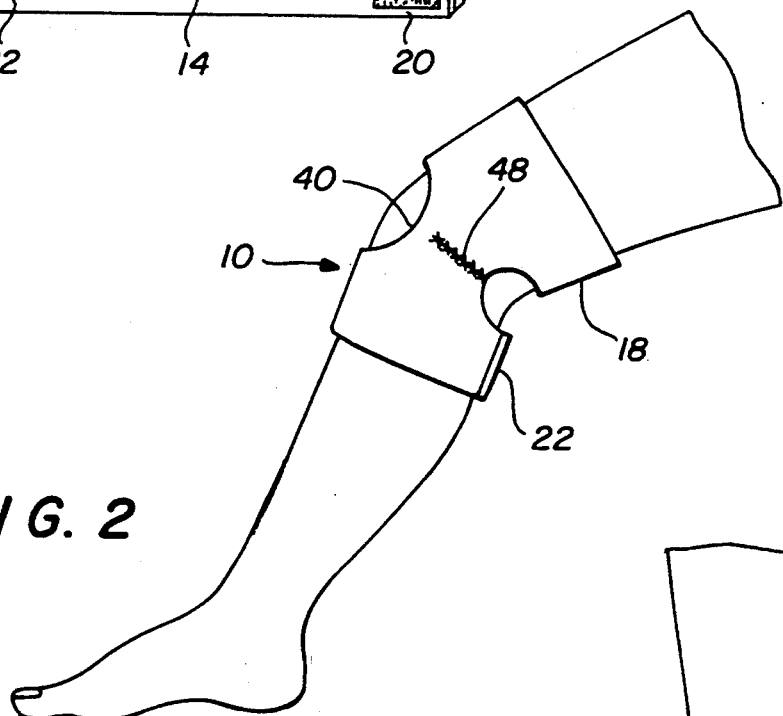
FIG. 2 illustrates a side view of the support in a natural resting, slightly-flexed position on a knee-joint.

FIG. 2 also shows that once the notch surfaces 44 and 46 are connected, the main body 10 of the support is no longer flat in an unloaded state. Rather, in its unloaded position, the knee-joint support holds the knee-joint in a slightly-flexed position. Any movement of the knee-joint from this slightly-flexed position, including extension, meets resistance from the knee-joint support.

Figure 3:
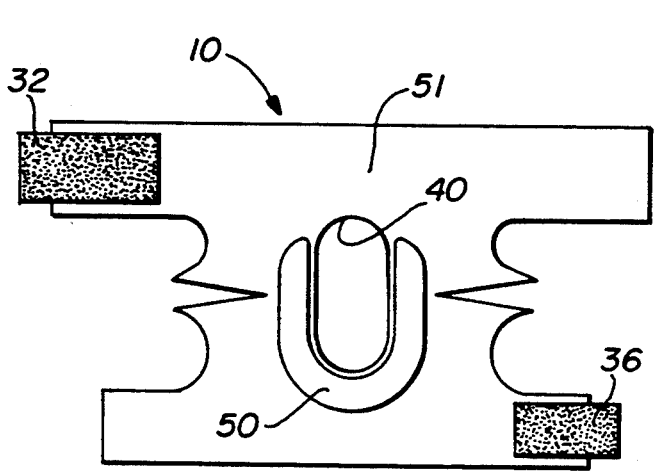
FIG. 3 illustrates an inside view of the main body of the knee-joint support showing the "U" shaped pad.
Figure 4:
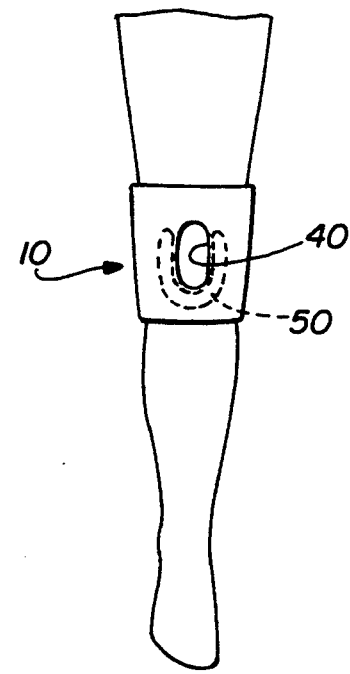
FIG. 4 illustrates a front view of the support in position on a knee-joint.

FIGS. 3 and 4 illustrate another feature of the present invention: a pad 50 attached to the inner surface 51 of the main body 10 of the knee-joint support, adjacent to the knee-cap aperture 40. In its preferred embodiment, this pad 50 is generally "U" shaped and is attached to the main body 10 of the support so that it partially encircles the right, left and lower sides of the aperture 40 in the web structure 24. This pad 50 serves several functions. Its primary function is to fill a gap caused by the natural contour of the knee-joint so that the support maintains contact and resistance to movement particularly in extension. The pad 50 also provides additional support to the Patella on both sides of the arthrodial joint without inhibiting the Patella's motion or applying undesired pressure to the front of the Patella, pushing it into the knee-joint. The pad 50 also provides additional protection to the knee-joint against impact on or around the Patella.

FIGS. 5 and 6 illustrate another embodiment of the present invention. A knee brace or support 52 is shown surrounding a user's leg 54. The brace 52 is similar to the construction of the brace 10 described in detail above except that an inflatable bladder 56 is shown in phantom. As can be seen in FIGS. 5 and 6 bladder 56 includes a generally oval or circular shaped bladder portion 58 that is designed to accept and encircle the Patella and allow for relatively unencumbered movement of the Patella along a gliding path of the arthrodial joint. The oval shaped portion 58 also provides additional support and cushioning to the Patellar tendon to protect the tendon against a blow against a hard surface. Bladder 56 also includes a pair of elongated stay portions 60 that span either side of leg 54 thereby giving lateral support to the knee-joint of leg 54. As can be seen, brace 52 also includes an aperture 62 which functions identically to the aperture 40 described above. It is further noted that brace 52 includes sewn notches 64 which are constructed and serve the same function as notches 42 and joint 48 described above. Also, notches 64 provide a form fit to brace 52 to more completely conform to the shape of a user's knee.

As can be most clearly seen in FIG. 7, the bladder 56 including the oval portion 58 and stays 60 preferably includes a plurality of weld spots 66. The bladder 56 is preferably formed of at least two layers of a flexible expandable plastic material such that there is a cavity formed between the two layers for receiving fluids such as air. The weld spots 66 prevent the bladder 56 from being over filled and also provide points at which the bladder 56 can bend or flex to more completely conform to the shape of a user's joint, in this case the knee of leg 54. Bladder 56 also preferably includes an integral pump 68 for pumping air into bladder 56. Pump 68 includes a balloon member 70 for pumping air through a valve 72 to inflate bladder 56. In addition, pump 68 preferably includes a relief valve 74 for allowing excess pressure built up inside bladder 56 to be released thereby enabling precise adjustment of bladder 56 for providing optimal cushioning and support of a user's joint. Bladder 56 also includes outer most tab portions 76 used to hold bladder 56 within a brace 52, as described below.

Figure 8:
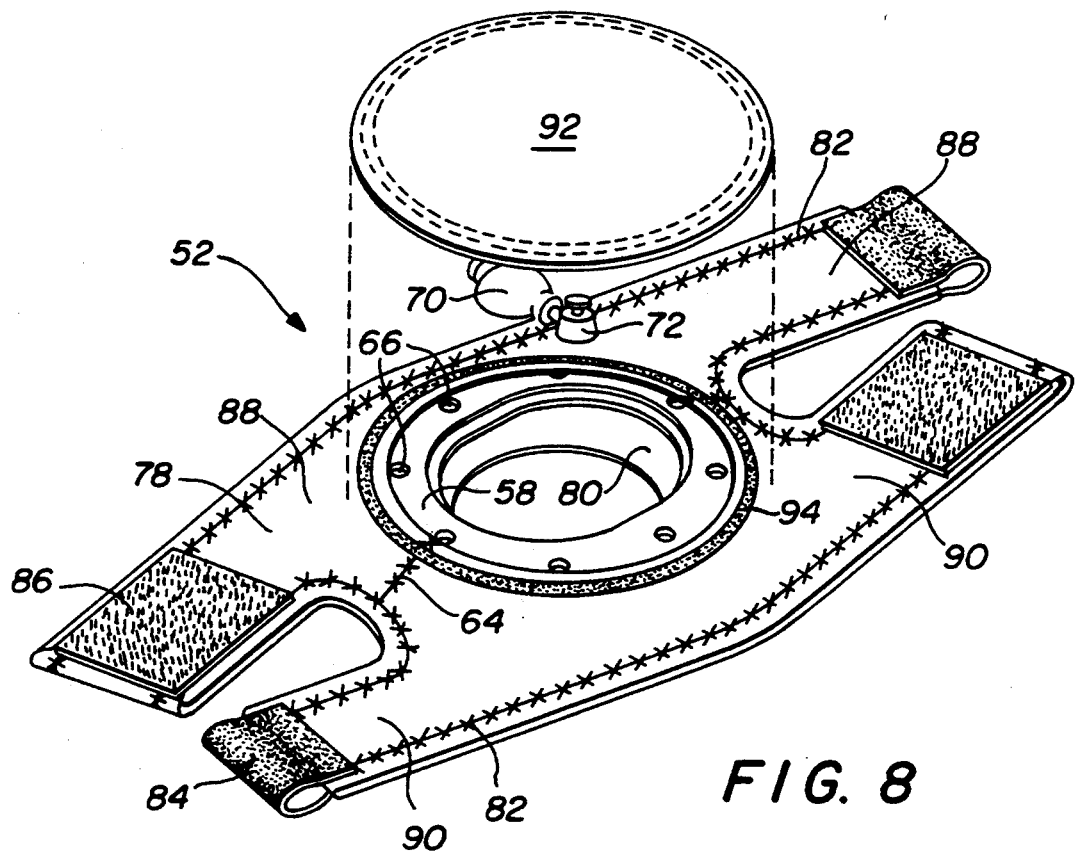
FIG. 8 illustrates another embodiment of the present invention with a detachable cap portion.

FIG. 8 shows brace 52 with an additional element to form an alternative embodiment of the present invention. Brace 52 includes two layers 78 and 80 of flexible resilient material similar to that used with support 10 above. The two layers are sewn together along seam 82 about the outer perimeter of brace 52. In order to hold bladder 56 within brace 52, tabs 76 extend within the brace 52 such that they overlap seam 82 so that when layers 78 and 80 are sewn together bladder 56 is held within brace 52. It is also noted that brace 52 includes hook and pile material 84 and 86, respectively. Similarly to support 10 above the hook and pile material is placed on opposite sides of each of the pair of flanges 88 and 90 such that there is an opposing pulling force relative to each other. This opposing pulling force helps to keep the brace 52 firmly held on leg 54 and helps prevent the brace 52 from turning about leg 54. The embodiment, shown in FIG. 8, further includes a cap portion 92, which is releasably attachable to brace 52 by hook material 94 and pile material (not shown) on cap 92.

Cap portion 92 enables the Patella area of leg 54 to be protected against injury. The cap portion 92 is preferably releasably attachable to brace 52 so that various types of cap portions 92 can be used with one brace 52 depending on the needs of the sport being played. This is advantageous because different sports may require different amounts and types of protection of the Patella area. For example, it may be beneficial to have cap portion 92 formed of a flexible resilient plastic material to provide protection against a significant impact of a Patella against a surface such as may be experienced in hockey or football. Or alternatively, cap portion 92 may be formed of a foam type of material to provide a soft cushion for landing against hard surfaces such as may be experienced in volleyball or the like. In this way a single brace 52 can be used in a multitude of athletic situations by simply replacing one cap portion 92 for another of different construction.

Figure 9:
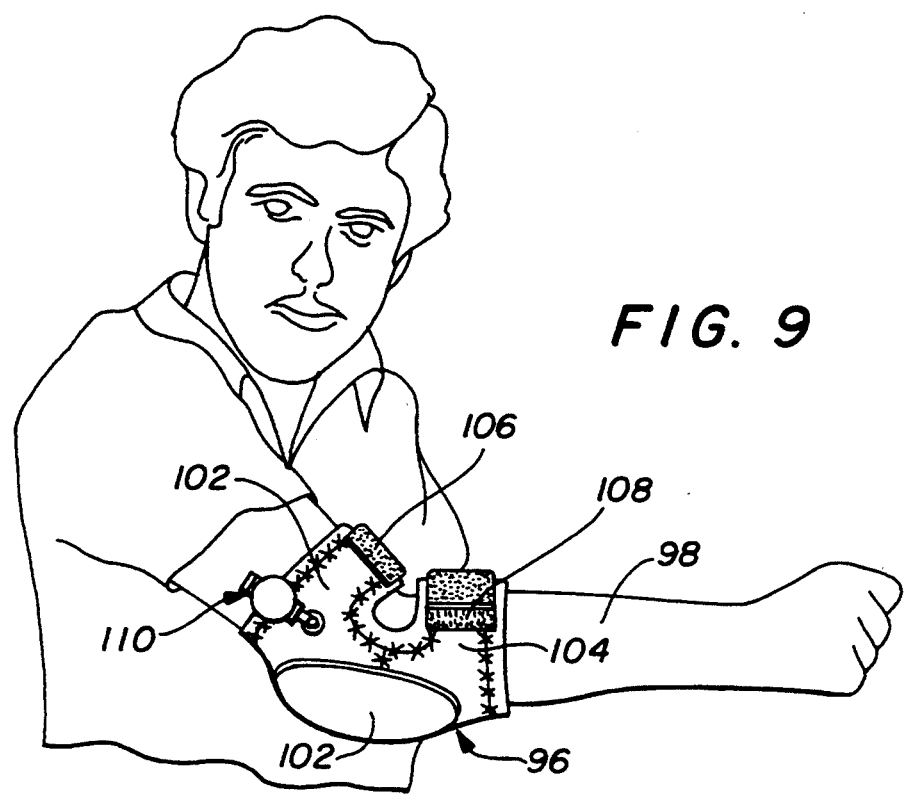
FIG. 9 illustrates another embodiment of the present invention applied to the elbow of a user.

FIG. 9 discloses a brace 96 for providing support to an elbow of an arm 98. Brace 96 is identical to brace 52 in all material respect except that the size of brace 96 is smaller to accommodate the arm 98 rather than leg 54. Brace 96 includes sewn notches 100 and flanges 102 and 104 with hook and pile material 106 and 108, respectively. Brace 96 further includes a pump 110, which is identical to pump 68, and a cap 112 which functions similarly to cap 92 described above. Brace 96 also includes a bladder (not shown) connected to pump 110 and secured within the brace for providing inflatable support to the elbow.

Figure 10:
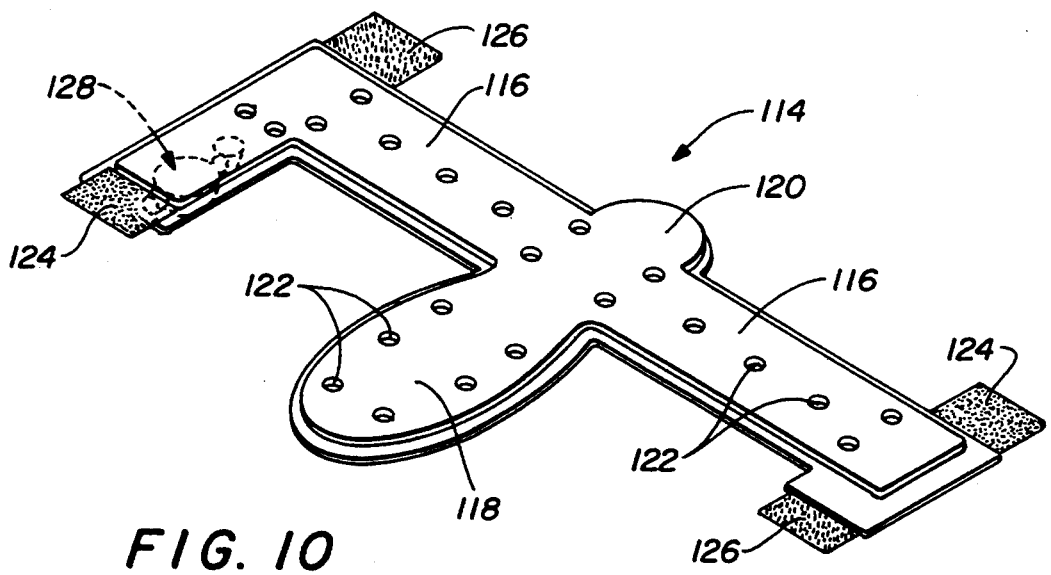
FIG. 10 illustrates another embodiment of the present invention for attachment to a foot of a user for providing lateral support to a user's ankle.

FIG. 10 discloses still a further embodiment of the present invention which includes an inflatable ankle brace 114. Ankle brace 114 includes a pair of elongated stay members 116 extending radially from a central bladder portion 118 having a shape generally conforming to the shape of the sole of a foot including a heel portion 120. Elongated stays are integrally formed with bladder portion 118 at each side of heel portion 120. The brace 114 includes plurality of weld spots 122 spaced throughout the stay portions 116 and foot portion 118. Similarly to the knee pad described above the weld spots provide flexibility to the brace to allow the user a significant amount of freedom of movement while still providing cushioning and support to the user's ankle. Brace 114 includes hook material 124 and pile material 126, in order to attach brace 114 to the user's lower leg. Brace 114 preferably includes a pump 128, which is identical to pump 68 above. In use, brace 114 preferably is of such constuction as to allow an athletic shoe to be worn over the brace 114 and still allow significant but restricted movement of the user's ankle and lower leg during athletic activity while providing lateral support to the ankle. Also, the foot portion 118 provides protection to a user's joints by softening the impact experienced during running and jumping by the user.

Figure 11:
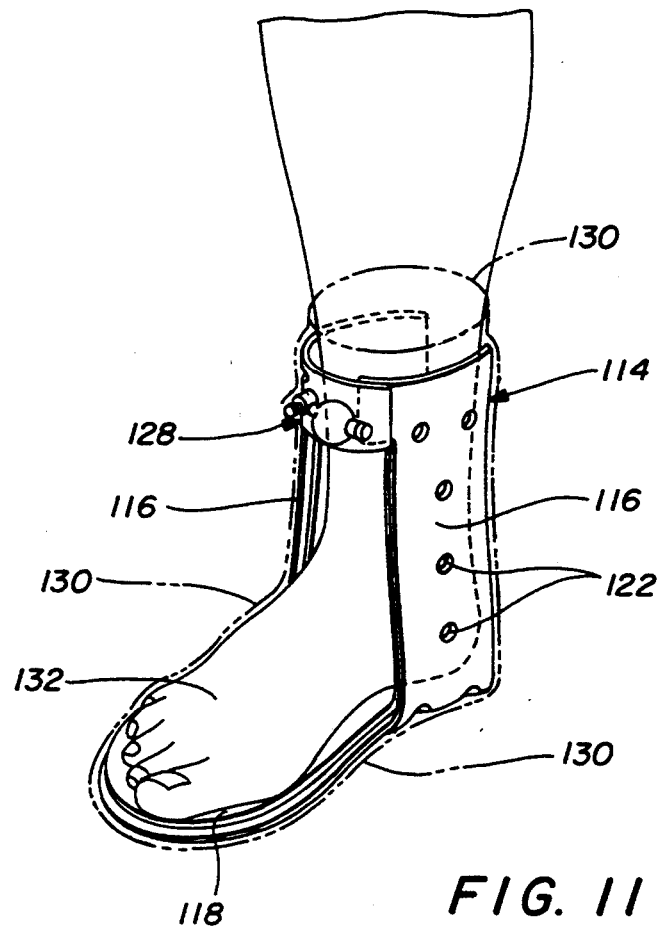
FIG. 11 illustrates another embodiment of the present invention wherein the bladder of FIG. 10 is surrounded by a flexible resilient sock.

FIG. 11 illustrates an alternate embodiment of the brace 114 and includes a sock 130 integrally formed with the brace 114. Sock 130 is preferably formed of a material such as neoprene or other flexible resilient material that generally conforms to the shape of the user's foot while providing some general support the user's ankle. The sock 130 is advantageous in that it provides a means for retaining the brace 114 securely about a user's foot, ankle, and lower leg.

The invention may be embodied in other specific forms without departing from its spirit or essential characteristics. The described embodiment is to be considered in all respects only as illustrative and not restrictive, and the scope of the invention is, therefore, indicated by the appended claims rather than the foregoing description. All changes that come within the meaning and range of equivalency of the claims are embraced within their scope.

I claim:

1. A brace for supporting and restricting movement of a joint of a limb of a user, the brace comprising:
    a main body formed of at least one layer of flexible, resilient material for providing support to and restricted movement of a joint of a user; attachment means connected to the main body for releasably attaching the brace to the user's joint;
    an inflatable bladder attached to the main body, said bladder consisting essentially of only two parallel arms and an integrally formed generally annular portion positioned between said parallel arms;
    said parallel arms for engaging only each side of the joint parallel to the limb when said brace is in use and said parallel arms providing lateral support to the user's joint when the parallel arms are applied to opposing sides of the user's joint parallel to the limb; and
    said generally annular portion adapted to substantially encircle the user's joint for additional adjustment support and cushioning to the user's joint.

2. The brace of claim 1 wherein the bladder includes a plurality of weld spots for providing flexibility to the bladder for allowing the bladder to conform to the shape of the user's joint.

3. The brace of claim 2 wherein the brace is shaped to conform to the user's knee or elbow joint.

4. The brace of claim 1, wherein the attachment means includes pairs of top and bottom flanges integral to the main body thereby forming a generally I-shaped brace wherein the flanges are adapted to be wrapped around the user's joint.

5. The brace of claim 4 wherein the pair of the top flanges is longer than the pair of bottom flanges.

6. The brace of claim 4 wherein the attachment means further includes mating portions of hook and pile fastening material attached to each of the top and bottom flange pairs.

7. The brace of claim 6 wherein the hook material of the top flange pair is attached to a flange on a side of the main body opposite from the hook material of the bottom flange pair for providing opposing forces between the top and bottom flange pairs for reducing rotation of the brace about the user's joint.

8. The brace of claim 4 further including:
a pair of notches, formed on opposite sides of the main body between the top and bottom flanges for positioning on each side of the user's joint, each of said notches being a generally V-shaped notch and each of said notches is closed by connecting the two sides of each notch together such that the brace generally conforms to the shape of the user's joint.

9. The brace of claim 1 further including: structure defining a central aperture in the main body;
a cap portion generally conforming to the shape of the main body aperture; and
attachment means for releasably attaching the cap portion to the main body for covering the main body aperture.

10. The brace of claim 9 wherein the cap portion is formed of a resilient plastic material.

11. The brace of claim 1 wherein the attachment means includes hook and pile material.

* * * * *